United States Patent [19]

Bäther

[11] Patent Number: 4,917,863

[45] Date of Patent: Apr. 17, 1990

[54] COLORIMETRIC GAS MEASURING DEVICE FOR CHLOROSILANES

[75] Inventor: Wolfgang Bäther, Lübeck, Fed. Rep. of Germany

[73] Assignee: Drägerwerk Aktiengesellschaft, Lübeck

[21] Appl. No.: 239,382

[22] Filed: Sep. 1, 1988

[30] Foreign Application Priority Data

Sep. 1, 1987 [DE] Fed. Rep. of Germany ....... 3729078

[51] Int. Cl.$^4$ .............................................. G01T 1/48
[52] U.S. Cl. ...................... 422/58; 422/59; 422/60; 422/86; 422/88
[58] Field of Search ............ 422/58, 88, 102, 59, 422/60, 86; 436/178, 72, 73, 74, 124, 181

[56] References Cited

U.S. PATENT DOCUMENTS

| | | | |
|---|---|---|---|
| 4,259,287 | 3/1981 | Leichnitz | 422/59 |
| 4,436,823 | 3/1984 | Blümcke et al. | 436/73 X |
| 4,478,792 | 10/1984 | McConnaughey et al. | 422/58 X |
| 4,692,309 | 9/1987 | Pannwitz | 422/88 X |
| 4,765,962 | 8/1988 | Heim | 422/88 X |
| 4,783,316 | 11/1988 | Pannwitz | 422/88 X |

Primary Examiner—Christine M. Nucker
Attorney, Agent, or Firm—Walter Ottesen

[57] ABSTRACT

The invention relates to a colorimetric gas measuring device having a porous substrate accessible to the air sample to be investigated. The substrate includes a conversion zone which converts a component to be detected into a substance which leads to a coloration of an indicator in a detection zone. The gas measuring device makes possible a simple and inexpensive quantitative detection of chlorosilanes. For this purpose, the conversion zone includes silica gel and the detection zone includes a carrier impregnated with an acid indicator.

18 Claims, 1 Drawing Sheet

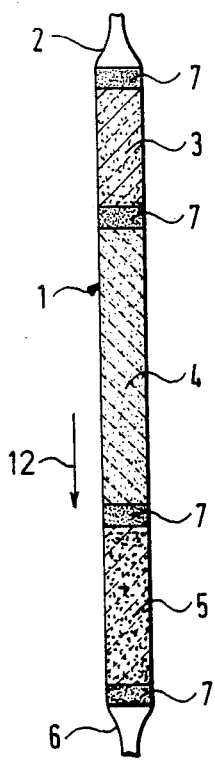
Fig. 1
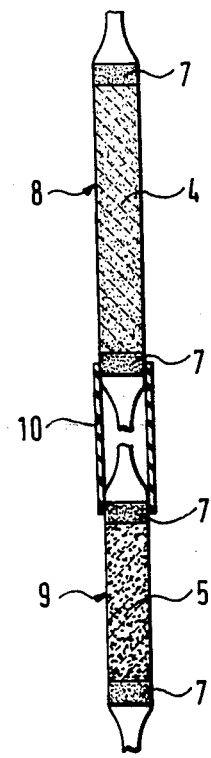
Fig. 2
Fig. 3
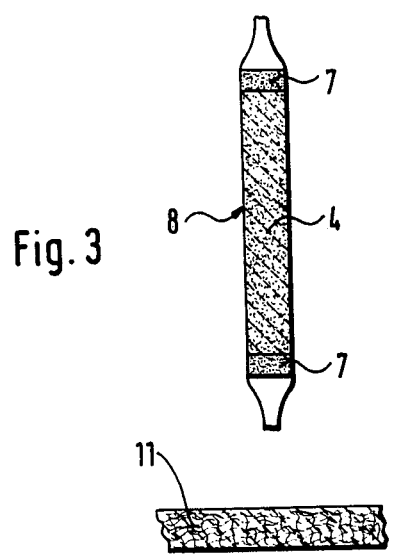

COLORIMETRIC GAS MEASURING DEVICE FOR CHLOROSILANES

FIELD OF THE INVENTION

The invention relates to a colorimetric gas measuring device having a porous substrate which is accessible to the air sample to be investigated. The substrate contains a conversion zone which converts a component to be detected into a substance which leads to a coloration of an indicator in a detection zone.

BACKGROUND OF THE INVENTION

Such a detector tube is disclosed in U.S. Pat. No. 4,259,287 and is equipped with a forward layer for quantitatively detecting NaOH aerosols and/or CaO aerosols. The forward layer is made of a carrier material impregnated with ammonium chloride on which the aerosol is liberated. A highly volatile reaction product is produced which is detected in an adjacent indicating layer impregnated with acid and bromophenol blue.

Chlorosilanes are used with ever increasing frequency in the manufacture of semiconductors so that the importance of their detection is ever increasing. However, no simple and convenient detection systems which are inexpensive to produce such as a detector tube are known.

SUMMARY OF THE INVENTION

In view of the foregoing, it is an object of the invention to provide a detector tube for quantitatively detecting chlorosilanes which is both simple and inexpensive.

According to a feature of the colorimetric gas measuring device of the invention, a conversion zone is provided for detecting chlorosilanes which includes a silica gel and a detecting zone having a carrier impregnated with an acid indicator.

The chlorosilanes penetrating the conversion zone from the ambient react with the silinol groups located on the surface of the silica gel and form silylene ethers and hydrogen chloride. The released hydrogen chloride can be detected with the aid of the acid indicator impregnated on the silica gel. A suitable acid indicator is, for example, bromophenol blue.

With the aid of such a detector tube, it is possible to detect chlorosilanes in a simple, reliable and inexpensive manner in that the length of the coloration zone of the acid indicator is measured.

According to an especially simple embodiment of the invention, the silica gel and the impregnated silica gel are mixed with each other as a porous filling of the detector tube. The released hydrogen chloride can then react directly with the acid indicator and a most rapid and complete indication is obtained since no adsorption losses occur. This is visible as an advancing coloration zone.

According to a further advantageous embodiment of the invention, the conversion zone can be configured as a forward layer and the detection zone as an adjacent indicating layer of the detector tube. In the same manner, the conversion zone can be configured as a forward tube and the detection zone as an indicator tube with these tubes being connected into the flow after they have been opened.

A tape device can also be used which has an indicator tape impregnated with an acid indicator. With these tape devices, the conversion zone can be configured as a charge of a forward tube through which the air sample is guided toward the indicator tape.

An especially simple configuration for a conversion zone and a detection zone is that the same silica gel carrier can be utilized which is impregnated with the acid indicator. The conversion of chlorosilanes occurs on the surface of the silica gel. The acid which forms can then react immediately with the acid indicator.

In the event that the air sample to be investigated already contains hydrogen chloride or similar gas components which influence the acid indicator, then a prefilter made of quartz glass can be placed ahead of the conversion zone with the quartz glass carrier being coated with a tertiary amine which is difficult to volatilize. In this way, all hydrogen chlorides contained in the air sample will be held back from the conversion zone so that a falsification of the measuring result can be precluded. A suitable amine for this purpose is triethylenediamine; however, tribenzylamine or bipyridine can also be utilized.

The conversion zone as well as the detection zone can be configured as a granular charge of a through-flow detector tube or also of a diffusion tube.

BRIEF DESCRIPTION OF THE DRAWINGS

The invention will now be described with reference to the drawings wherein:

FIG. 1 is a side elevation view, in section, of a through-flow detector tube according to an embodiment of the invention;

FIG. 2 is an elevation view, in section, of another embodiment of the colorimetric gas measuring device according to the invention; and, FIG. 3 is a schematic of another embodiment of the invention wherein a forward tube is mounted ahead of the indicator tape of a tape device.

DESCRIPTION OF THE PREFERRED EMBODIMENTS OF THE INVENTION

The through-flow detector tube 1 shown in FIG. 1 has respective ends which can be snapped off to open the tube to permit a through flow of the air sample to be investigated. The detector tube includes a prefilter 3 at its one end 2 opened to receive the air sample. The prefilter 3 comprises a quartz glass carrier coated with a tertiary amine. A conversion zone of silica gel configured as a forward layer 4 is disposed downstream of the prefilter 3 with the flow direction being indicated by arrow 12. A detection zone in the form of an indicator layer 5 follows the forward layer 4 and comprises a silica gel charge impregnated with an acid indicator. The prefilter 3 and the indicator layer 5 are separated from the respective open ends (2, 6) of the detector tube by means of porous holders 7. Further porous holders 7 partition the forward layer 4 from the indicator layer 5 and from the prefilter 3.

Referring to FIG. 2, a forward tube 8 is filled with a forward layer 4 and a further detector tube 9 is provided with an indicator layer 5. Both opened tubes (8, 9) are interconnected with a tube segment 10 so that the conversion substance flowing out of the forward tube 8 can be conducted into the detector tube 9 which follows the forward tube 8.

In FIG. 3, the forward tube 8 is directed toward an indicator tape 11 of a tape detecting device for the colorimetric detection of contaminants with the indicator tape 11 being in the form of a detection zone impregnated with an acid indicator.

It is understood that the foregoing description is that of the preferred embodiments of the invention and that various changes and modifications may be made thereto without departing from the spirit and scope of the invention as defined in the appended claims.

What is claimed is:

1. A colorimetric gas measuring device for detecting chlorosilanes in an air sample, the device comprising:
    a housing having an openable inlet end and an openable outlet end so as to permit a flow of the air sample therethrough;
    a porous substrate disposed in said housing and accessible to the air sample entering the housing at said inlet end to be investigated as to the presence of chlorosilanes;
    said substrate being a conversion zone defined by unimpregnated silica gel for reacting directly with the chlorosilanes to form a detectable substance; and,
    a carrier impregnated with an acid indicator disposed downstream of said substrate to define a detection zone wherein said detectable substance reacts with said acid indicator to provide a colorimetric indication of the presence of the chlorosilanes.

2. A colorimetric gas measuring device for detecting chlorosilanes in an air sample, the device comprising:
    a tubular housing having an openable inlet end and an openable outlet end so as to permit a flow of the air sample therethrough;
    a porous substrate disposed in said housing and accessible to the air sample entering the housing at said inlet end to be investigated as to the presence of chlorosilanes;
    said substrate being a conversion zone defined by unimpregnated silica gel for reacting directly with the chlorosilanes to form a detectable substance; and,
    a carrier impregnated with an acid indicator also disposed in said housing to define a detection zone wherein said detectable substance reacts with said acid indicator to provided a colorimetric indication of the presence of the chlorosilanes and passes through said outlet to the ambient;
    said carrier being a silica gel impregnated with said acid indicator; and,
    said silica gel of said conversion zone and said silica gel of said detection zone being mixed to define a porous filling disposed in said tubular housing.

3. The colorimetric gas measuring device of claim 1, said porous substrate of said conversion zone being a forward layer disposed in said tubular housing; and, said carrier being a porous indicating layer disposed downstream of said forward layer.

4. A colorimetric gas measuring device for detecting chlorosilanes in an air sample, the device comprising: a forward tube having an openable inlet end and an openable outlet end so as to permit a flow of the air sample therethrough;
    an indicator tube openable at both of its ends and arranged downstream of said forward tube;
    a porous substrate disposed in said forward tube and accessible to the air sample entering said forward tube at said inlet end to be investigated as to the presence of chlorosilanes;
    said substrate being a conversion zone defined by unimpregnated silica gel for reacting directly with the chlorosilanes to form a detectable substance; and,
    a carrier impregnated with an acid indicator disposed in said indicator tube downstream of said substrate to define a detection zone wherein said detectable substance reacts with said acid indicator to provide a colorimetric indication of the presence of the chlorosilanes; and,
    a connecting piece for interconnecting said tubes after said ends have been opened for establishing a flow connection therebetween.

5. A colorimetric gas measuring device for detecting chlorosilanes in an air sample, the device comprising:
    a forward tube having an openable inlet end and an openable outlet end so as to permit a flow of the air sample therethrough;
    a porous substrate disposed in said forward tube and accessible to the air sample entering the tube at said inlet end to be investigated as to the presence of chlorosilanes;
    said substrate being a conversion zone defined by unimpregnated silica gel for reacting directly with the chlorosilanes to form a detectable substance;
    a carrier impregnated with an acid indicator disposed downstream of said substrate to define a detection zone wherein said detectable substance reacts with said acid indicator to provide a colorimetric indication of the presence of the chlorosilanes;
    said carrier being an indicator tape impregnated with said acid indicator to define said detection zone; and,
    said indicator tape being disposed downstream of said forward tube.

6. The colorimetric gas measuring device of claim 1, said silica gel of said conversion zone also being said carrier of said detection zone.

7. The colorimetric gas measuring device of claim 1, said acid indicator being bromophenol blue.

8. The colorimetric gas measuring device of claim 1, further comprising a prefilter disposed ahead of said conversion zone and including a carrier made of quartz glass and coated with tertiary amine which is difficult to volatize.

9. The colorimetric gas measuring device of claim 8, said tertiary amine being triethylenediamine (1, 4-diazabicyclo (2,2,2) octane).

10. The colorimetric gas measuring device of claim 1, said carrier being a silica gel impregnated with said acid indicator.

11. A colorimetric gas measuring device for detecting chlorosilanes in an air sample, the device comprising:
    a housing having an openable inlet end to permit a flow of the air sample thereinto;
    a porous substrate disposed in said housing and accessible to the air sample entering the housing at said inlet end to be investigated as to the presence of chlorosilanes;
    said substrate being a conversion zone defined by unimpregnated silica gel for reacting directly with the chlorosilanes to form a detectable substance; and,
    a carrier impregnated with an acid indicator disposed adjacent said substrate to define a detection zone wherein said detectable substance reacts with said acid indicator to provide a colorimetric indication of the presence of the chlorosilanes.

12. The colorimetric gas measuring device of claim 11, said carrier being a silica gel impregnated with said acid indicator.

13. The colorimetric gas measuring device of claim 11, further comprising: a prefilter disposed ahead of said conversion zone and including a carrier made of quartz glass and coated with tertiary amine which is difficult to volatize.

14. A colorimetric gas measuring device for detecting chlorosilanes in an air sample, the device comprising:
   a housing having an openable inlet end to permit a flow of the air sample thereinto;
   a porous substrate disposed in said housing and accessible to the air sample entering the housing at said inlet end to be investigated as to the presence of chlorosilanes;
   said substrate being a conversion zone defined by unimpregnated silica gel for reacting directly with the chlorosilanes to form a detectable substance; and,
   a carrier impregnated with an acid indicator also disposed in said housing to define a detection zone wherein said detectable substance reacts with said acid indicator to provide a colorimetric indication of the presence of the chlorosilanes;
   said carrier being a silica gel impregnated with said acid indicator; and,
   said silica gel of said conversion zone and said silica gel of said detection zone being mixed to define a porous filling disposed in said tubular housing.

15. The colorimetric gas measuring device of claim 14, further comprising: a prefilter disposed ahead of said conversion zone and including a carrier made of quartz glass and coated with tertiary amine which is difficult to volatize.

16. A method of detecting chlorosilanes in an air sample, the method comprising the steps of:
   passing the air sample over a porous substrate in the form of a conversion layer defined by unimpregnated silica gel for reacting directly with the chlorosilanes to form a detectable substance; and,
   then passing said detectable substance over a carrier impregnated with an acid indicator defining a detection zone wherein said detectable substance reacts with said acid indicator to provide a colorimetric indication of the presence of the chlorosilanes.

17. The method of claim 16, wherein: said carrier is a silica gel impregnated with said acid indicator.

18. The method of claim 17, wherein: said silica gel of said conversion zone and said silica gel of said detection zone are mixed to define a porous filling disposed in a tubular housing.

* * * * *